US008221420B2

(12) United States Patent
Keller (10) Patent No.: US 8,221,420 B2
(45) Date of Patent: Jul. 17, 2012

(54) TRAUMA NAIL ACCUMULATOR

(75) Inventor: Jason Keller, Orlando, FL (US)

(73) Assignee: AOI Medical, Inc., Orlando, FL (US)

( * ) Notice: Subject to any disclaimer, the term of this patent is extended or adjusted under 35 U.S.C. 154(b) by 31 days.

(21) Appl. No.: 12/706,268

(22) Filed: Feb. 16, 2010

(65) Prior Publication Data

US 2010/0241122 A1    Sep. 23, 2010

Related U.S. Application Data

(60) Provisional application No. 61/152,866, filed on Feb. 16, 2009.

(51) Int. Cl.
*A61B 17/68* (2006.01)
(52) U.S. Cl. ........................................................ 606/63
(58) Field of Classification Search .................. 606/192, 606/79, 80, 63, 62, 64, 68; 604/96.01, 103.07, 604/103.08, 103.13, 103.14
See application file for complete search history.

(56) References Cited

U.S. PATENT DOCUMENTS

| 1,685,380 | A | 9/1928 | Schultz |
| 3,030,951 | A | 4/1962 | Mandarino |
| 3,112,743 | A | 12/1963 | Cochran et al. |
| 3,320,957 | A | 5/1967 | Sokolik |
| 4,065,817 | A | 1/1978 | Branemark et al. |
| 4,313,434 | A | 2/1982 | Segal |
| 4,369,772 | A | 1/1983 | Miller |
| 4,403,606 | A | 9/1983 | Woo et al. |
| 4,403,607 | A | 9/1983 | Woo et al. |
| 4,493,317 | A | 1/1985 | Klaue |
| 4,494,535 | A | 1/1985 | Haig |
| 4,503,848 | A | 3/1985 | Caspar et al. |
| 4,513,744 | A | 4/1985 | Klaue |
| 4,653,489 | A | 3/1987 | Tronzo |
| 4,743,260 | A | 5/1988 | Burton |
| 4,751,922 | A | 6/1988 | DiPietropolo |
| 4,773,406 | A | 9/1988 | Spector et al. |
| 4,794,918 | A | 1/1989 | Wolter |
| 4,969,888 | A | 11/1990 | Scholter et al. |
| 5,002,544 | A | 3/1991 | Klaue et al. |
| 5,014,124 | A | 5/1991 | Fujisawa |

(Continued)

FOREIGN PATENT DOCUMENTS

DE    39 14164    1/1991

(Continued)

OTHER PUBLICATIONS

International Search Report dated Mar. 21, 2007 for Application No. PCT/US06/044443.
International Search Report and Written Opinion dated Jun. 10, 2009 for Application No. PCT/US2008/064312.
Office Action dated Nov. 16, 2009 for U.S. Appl. No. 11/600,313.

(Continued)

*Primary Examiner* — Pedro Philogene
(74) *Attorney, Agent, or Firm* — Ulmer & Berne LLP (57) ABSTRACT

Provided is an accumulator that may store energy within a pressurized inflatable nail to compensate for small changes or losses in a system volume. Alternatively, the accumulator may be external to a pressurized inflatable nail and attached to the nail after the nail is implanted. The accumulator may be comprise a piston or a pressurized bladder. The energy may be stored in a spring, compressed air, or other pressure source. The accumulator may stabilize a system pressure by supplying fluid to the closed system. Alternatively, the accumulator may stabilize a system pressure by replacing the volume of the lost fluid.

19 Claims, 10 Drawing Sheets

U.S. PATENT DOCUMENTS

| | | |
|---|---|---|
| 5,019,078 A | 5/1991 | Perren et al. |
| 5,030,201 A | 7/1991 | Palestrant |
| 5,053,036 A | 10/1991 | Perren et al. |
| 5,062,845 A | 11/1991 | Kuslich et al. |
| 5,085,660 A | 2/1992 | Lin |
| 5,102,413 A | 4/1992 | Poddar |
| 5,108,404 A | 4/1992 | Scholten et al. |
| 5,118,338 A | 6/1992 | Moller |
| 5,147,361 A | 9/1992 | Ojima et al. |
| 5,151,103 A | 9/1992 | Tepic et al. |
| 5,211,651 A | 5/1993 | Reger et al. |
| 5,275,601 A | 1/1994 | Gogolewski et al. |
| 5,303,718 A | 4/1994 | Krajicek |
| 5,344,421 A | 9/1994 | Crook |
| 5,360,432 A | 11/1994 | Shturman |
| 5,364,399 A | 11/1994 | Lowery et al. |
| 5,376,100 A | 12/1994 | Lefebvre |
| 5,402,772 A * | 4/1995 | Moll et al. ................... 600/207 |
| 5,403,136 A | 4/1995 | Mathys |
| 5,403,317 A | 4/1995 | Bonutti |
| 5,423,850 A | 6/1995 | Berger |
| 5,431,671 A | 7/1995 | Nallakrishnan |
| 5,445,639 A | 8/1995 | Kuslich et al. |
| 5,480,400 A | 1/1996 | Berger |
| 5,490,859 A | 2/1996 | Mische et al. |
| 5,514,137 A | 5/1996 | Coutts |
| 5,527,311 A | 6/1996 | Procter et al. |
| 5,540,707 A | 7/1996 | Ressemann et al. |
| 5,549,612 A | 8/1996 | Yapp et al. |
| 5,549,679 A | 8/1996 | Kuslich |
| 5,556,429 A | 9/1996 | Felt |
| 5,562,672 A | 10/1996 | Huebner et al. |
| 5,571,189 A | 11/1996 | Kuslich |
| 5,591,170 A | 1/1997 | Spievack et al. |
| 5,607,426 A | 3/1997 | Ralph et al. |
| 5,613,967 A | 3/1997 | Engelhardt et al. |
| 5,616,144 A | 4/1997 | Yapp et al. |
| 5,658,310 A | 8/1997 | Berger |
| 5,665,110 A | 9/1997 | Chervitz et al. |
| 5,674,296 A | 10/1997 | Bryan et al. |
| 5,681,310 A | 10/1997 | Yuan et al. |
| 5,681,311 A | 10/1997 | Foley et al. |
| 5,693,011 A | 12/1997 | Onik |
| 5,695,513 A | 12/1997 | Johnson et al. |
| 5,709,686 A | 1/1998 | Talos et al. |
| 5,720,749 A | 2/1998 | Rupp |
| 5,733,287 A | 3/1998 | Tepic et al. |
| 5,735,853 A | 4/1998 | Olerud |
| 5,766,176 A | 6/1998 | Duncan |
| 5,772,662 A | 6/1998 | Chapman et al. |
| 5,800,433 A | 9/1998 | Benzel et al. |
| 5,807,396 A | 9/1998 | Raveh |
| 5,827,289 A | 10/1998 | Reiley et al. |
| 5,843,103 A | 12/1998 | Wulfman |
| 5,871,486 A | 2/1999 | Huebner et al. |
| 5,888,220 A | 3/1999 | Felt et al. |
| 5,891,145 A | 4/1999 | Morrison et al. |
| 5,904,683 A | 5/1999 | Pohndorf et al. |
| 5,925,056 A | 7/1999 | Thomas et al. |
| 5,928,239 A | 7/1999 | Mirza |
| 5,935,131 A | 8/1999 | Bonutti |
| 5,964,762 A | 10/1999 | Biedermann et al. |
| 5,972,015 A | 10/1999 | Scribner et al. |
| 5,990,194 A | 11/1999 | Dunn et al. |
| 6,017,345 A | 1/2000 | Richelsoph |
| 6,019,776 A | 2/2000 | Preissman |
| 6,022,350 A | 2/2000 | Ganem |
| 6,030,389 A | 2/2000 | Wagner et al. |
| 6,033,411 A | 3/2000 | Preissman |
| 6,048,343 A | 4/2000 | Mathis et al. |
| 6,048,346 A | 4/2000 | Reiley et al. |
| 6,066,154 A | 5/2000 | Reiley et al. |
| 6,071,284 A | 6/2000 | Fox |
| 6,083,672 A | 7/2000 | Roefs et al. |
| 6,096,054 A | 8/2000 | Wyzgala et al. |
| 6,127,597 A | 10/2000 | Beyar et al. |
| 6,139,509 A | 10/2000 | Yuan et al. |
| 6,140,452 A | 10/2000 | Felt et al. |
| 6,171,312 B1 | 1/2001 | Beaty |
| 6,210,376 B1 | 4/2001 | Grayson |
| 6,214,012 B1 | 4/2001 | Karpman et al. |
| 6,221,029 B1 | 4/2001 | Mathis et al. |
| 6,224,600 B1 * | 5/2001 | Protogirou ................... 606/63 |
| 6,224,604 B1 | 5/2001 | Suddaby |
| 6,231,615 B1 | 5/2001 | Preissman |
| 6,235,043 B1 | 5/2001 | Reiley et al. |
| 6,238,391 B1 | 5/2001 | Olsen et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,264,659 B1 | 7/2001 | Ross et al. |
| 6,273,916 B1 | 8/2001 | Murphy |
| 6,280,456 B1 | 8/2001 | Scribner et al. |
| 6,283,971 B1 | 9/2001 | Temeles |
| 6,296,639 B1 | 10/2001 | Truckai et al. |
| 6,309,420 B1 | 10/2001 | Preissman |
| 6,348,055 B1 | 2/2002 | Preissman |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,423,083 B2 | 7/2002 | Reiley et al. |
| 6,425,887 B1 | 7/2002 | McGuckin et al. |
| 6,425,923 B1 | 7/2002 | Stalcup et al. |
| 6,440,138 B1 | 8/2002 | Reiley et al. |
| 6,447,514 B1 | 9/2002 | Stalcup et al. |
| 6,450,973 B1 | 9/2002 | Murphy |
| 6,488,667 B1 | 12/2002 | Murphy |
| 6,494,535 B2 | 12/2002 | Galbreath |
| 6,558,386 B1 | 5/2003 | Cragg |
| 6,558,390 B2 | 5/2003 | Cragg |
| 6,558,396 B1 | 5/2003 | Inoue |
| 6,565,572 B2 | 5/2003 | Chappins |
| 6,575,979 B1 | 6/2003 | Cragg |
| 6,582,439 B1 | 6/2003 | Sproul |
| 6,582,446 B1 | 6/2003 | Marchosky |
| 6,592,559 B1 | 7/2003 | Pakter et al. |
| 6,595,998 B2 | 7/2003 | Johnson et al. |
| 6,599,520 B2 | 7/2003 | Scarborough et al. |
| 6,607,544 B1 | 8/2003 | Boucher et al. |
| 6,613,018 B2 | 9/2003 | Bagga et al. |
| 6,613,054 B2 | 9/2003 | Scribner et al. |
| 6,613,089 B1 | 9/2003 | Estes et al. |
| 6,620,162 B2 | 9/2003 | Kuslich et al. |
| 6,626,903 B2 | 9/2003 | McGuckin, Jr. et al. |
| 6,632,235 B2 | 10/2003 | Weikel et al. |
| 6,641,587 B2 | 11/2003 | Scribner et al. |
| 6,645,213 B2 | 11/2003 | Saud et al. |
| 6,652,568 B1 | 11/2003 | Becker et al. |
| 6,663,647 B2 | 12/2003 | Reiley et al. |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,886 B2 | 1/2004 | Weikel et al. |
| 6,685,718 B1 | 2/2004 | Wyzgala et al. |
| 6,689,132 B2 | 2/2004 | Biscup |
| 6,699,242 B2 | 3/2004 | Heggeness |
| 6,706,069 B2 | 3/2004 | Berger |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,746,451 B2 | 6/2004 | Middleton et al. |
| 6,749,595 B1 | 6/2004 | Murphy |
| 6,752,791 B2 | 6/2004 | Murphy et al. |
| 6,752,809 B2 | 6/2004 | Gorek |
| 6,758,855 B2 | 7/2004 | Fulton, III et al. |
| 6,758,863 B2 | 7/2004 | Estes et al. |
| 6,770,079 B2 | 8/2004 | Bhatnagar et al. |
| 6,780,191 B2 | 8/2004 | Sproul |
| 6,790,210 B1 | 9/2004 | Cragg et al. |
| 6,805,697 B1 | 10/2004 | Helm et al. |
| 6,814,734 B2 | 11/2004 | Chappuis et al. |
| 6,832,988 B2 | 12/2004 | Sproul |

| Patent Number | Date | Inventor |
|---|---|---|
| 6,843,796 B2 | 1/2005 | Harari et al. |
| 6,852,095 B1 | 2/2005 | Ray |
| 6,863,672 B2 | 3/2005 | Reiley et al. |
| 6,869,445 B1 | 3/2005 | Johnson |
| 6,887,246 B2 | 5/2005 | Bhatnagar et al. |
| 6,899,716 B2 | 5/2005 | Cragg |
| 6,902,547 B2 | 6/2005 | Aves et al. |
| 6,916,308 B2 | 7/2005 | Dixon et al. |
| 6,921,403 B2 | 7/2005 | Cragg et al. |
| 6,923,813 B2 | 8/2005 | Phillips et al. |
| 6,932,843 B2 | 8/2005 | Smith et al. |
| 6,939,351 B2 | 9/2005 | Eckman |
| 6,960,215 B2 | 11/2005 | Olson, Jr. et al. |
| 6,960,900 B2 | 11/2005 | Fogarty et al. |
| 6,979,341 B2 | 12/2005 | Scribner et al. |
| 6,979,352 B2 | 12/2005 | Reynolds |
| 6,981,981 B2 | 1/2006 | Reiley et al. |
| 6,984,063 B2 | 1/2006 | Barker et al. |
| 7,001,342 B2 | 2/2006 | Faciszewski |
| 7,008,433 B2 | 3/2006 | Voellmicke et al. |
| 7,014,633 B2 | 3/2006 | Cragg |
| 7,044,954 B2 | 5/2006 | Reiley et al. |
| 7,056,321 B2 | 6/2006 | Pagliuca et al. |
| 7,077,865 B2 | 7/2006 | Bao et al. |
| 7,087,058 B2 | 8/2006 | Cragg |
| 7,114,501 B2 | 10/2006 | Johnson et al. |
| 7,144,397 B2 | 12/2006 | Lambrecht et al. |
| 7,153,305 B2 | 12/2006 | Johnson et al. |
| 7,153,307 B2 | 12/2006 | Scribner et al. |
| 7,156,860 B2 | 1/2007 | Wallsten |
| 7,156,861 B2 | 1/2007 | Scribner et al. |
| 7,160,306 B2 | 1/2007 | Matsuzaki et al. |
| 7,226,481 B2 | 6/2007 | Kuslich |
| 7,234,468 B2 | 6/2007 | Johnson et al. |
| 7,238,209 B2 | 7/2007 | Matsuzaki et al. |
| 7,241,297 B2 | 7/2007 | Shaolian et al. |
| 7,241,303 B2 | 7/2007 | Reiss et al. |
| 7,252,671 B2 | 8/2007 | Scribner et al. |
| 7,252,686 B2 | 8/2007 | Carrison et al. |
| 7,295,868 B2 | 11/2007 | Bascle et al. |
| 7,295,869 B2 | 11/2007 | Bascle et al. |
| 7,309,338 B2 | 12/2007 | Cragg |
| 7,318,826 B2 | 1/2008 | Teitelbaum et al. |
| 7,326,203 B2 | 2/2008 | Papineau et al. |
| 7,329,259 B2 | 2/2008 | Cragg |
| 7,346,385 B2 | 3/2008 | Bascle et al. |
| 7,399,739 B2 | 7/2008 | Shimp |
| 7,473,256 B2 | 1/2009 | Assell et al. |
| 7,476,226 B2 | 1/2009 | Weikel et al. |
| 7,488,320 B2 | 2/2009 | Middleton |
| 7,488,337 B2 * | 2/2009 | Saab et al. ............... 606/192 |
| 7,491,236 B2 | 2/2009 | Cragg et al. |
| 7,500,977 B2 | 3/2009 | Assell et al. |
| 7,510,579 B2 | 3/2009 | Preissman |
| 7,530,993 B2 | 5/2009 | Assell et al. |
| 7,534,245 B2 | 5/2009 | Chappuis |
| 7,534,256 B2 | 5/2009 | Cragg |
| 7,540,875 B2 | 6/2009 | Jessen |
| 7,544,196 B2 | 6/2009 | Bagga et al. |
| 7,547,324 B2 | 6/2009 | Cragg et al. |
| 7,553,659 B2 | 6/2009 | Brodeur et al. |
| 7,555,343 B2 | 6/2009 | Bleich |
| 7,569,056 B2 | 8/2009 | Cragg et al. |
| 7,572,263 B2 | 8/2009 | Preissman |
| 7,588,574 B2 | 9/2009 | Assell et al. |
| 7,591,822 B2 | 9/2009 | Olson, Jr. et al. |
| 7,811,284 B2 * | 10/2010 | Rabiner et al. ............. 606/62 |
| 2001/0011174 A1 | 8/2001 | Reiley et al. |
| 2002/0026195 A1 | 2/2002 | Layne et al. |
| 2002/0029047 A1 | 3/2002 | Bascle et al. |
| 2002/0032444 A1 | 3/2002 | Mische |
| 2002/0068974 A1 | 6/2002 | Kuslich et al. |
| 2002/0116064 A1 | 8/2002 | Middleton |
| 2002/0188300 A1 | 12/2002 | Arramon et al. |
| 2003/0009208 A1 | 1/2003 | Snyder et al. |
| 2003/0032929 A1 | 2/2003 | McGuckin, Jr. |
| 2003/0032963 A1 | 2/2003 | Reiss et al. |
| 2003/0074075 A1 | 4/2003 | Thomas, Jr. et al. |
| 2003/0105469 A1 | 6/2003 | Karmon |
| 2003/0130664 A1 | 7/2003 | Boucher et al. |
| 2003/0135237 A1 | 7/2003 | Cragg et al. |
| 2003/0171812 A1 | 9/2003 | Grunberg et al. |
| 2003/0191474 A1 | 10/2003 | Cragg et al. |
| 2003/0191489 A1 | 10/2003 | Reiley et al. |
| 2003/0204189 A1 | 10/2003 | Cragg |
| 2003/0220648 A1 | 11/2003 | Osorio et al. |
| 2003/0229372 A1 | 12/2003 | Reiley et al. |
| 2003/0233096 A1 | 12/2003 | Osorio et al. |
| 2004/0010263 A1 | 1/2004 | Boucher et al. |
| 2004/0019354 A1 | 1/2004 | Johnson et al. |
| 2004/0024409 A1 | 2/2004 | Sand et al. |
| 2004/0024410 A1 | 2/2004 | Olson et al. |
| 2004/0024463 A1 | 2/2004 | Thomas, Jr. et al. |
| 2004/0049202 A1 | 3/2004 | Berger |
| 2004/0068242 A1 | 4/2004 | McGuckin, Jr. |
| 2004/0073139 A1 | 4/2004 | Hirsch et al. |
| 2004/0087956 A1 | 5/2004 | Weikel et al. |
| 2004/0097930 A1 | 5/2004 | Justis et al. |
| 2004/0098015 A1 | 5/2004 | Weikel et al. |
| 2004/0102774 A1 | 5/2004 | Trieu |
| 2004/0122438 A1 | 6/2004 | Abrams |
| 2004/0153064 A1 | 8/2004 | Foley et al. |
| 2004/0153115 A1 | 8/2004 | Reiley et al. |
| 2004/0167561 A1 | 8/2004 | Boucher et al. |
| 2004/0167562 A1 | 8/2004 | Osorio et al. |
| 2004/0210231 A1 | 10/2004 | Boucher et al. |
| 2004/0210297 A1 | 10/2004 | Lin et al. |
| 2004/0215197 A1 | 10/2004 | Smith et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0267269 A1 | 12/2004 | Middleton et al. |
| 2005/0015148 A1 | 1/2005 | Jansen et al. |
| 2005/0038514 A1 | 2/2005 | Helm et al. |
| 2005/0043737 A1 | 2/2005 | Reiley et al. |
| 2005/0055097 A1 | 3/2005 | Grunberg et al. |
| 2005/0090852 A1 | 4/2005 | Layne et al. |
| 2005/0113919 A1 | 5/2005 | Cragg et al. |
| 2005/0113929 A1 | 5/2005 | Cragg et al. |
| 2005/0119662 A1 | 6/2005 | Reiley et al. |
| 2005/0124989 A1 | 6/2005 | Suddaby |
| 2005/0131267 A1 | 6/2005 | Talmadge |
| 2005/0131268 A1 | 6/2005 | Talmadge |
| 2005/0137601 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0149049 A1 | 7/2005 | Assell et al. |
| 2005/0182417 A1 | 8/2005 | Pagano |
| 2005/0187556 A1 | 8/2005 | Stack et al. |
| 2005/0203527 A1 | 9/2005 | Carrison et al. |
| 2005/0261695 A1 | 11/2005 | Cragg et al. |
| 2006/0004369 A1 | 1/2006 | Patel et al. |
| 2006/0116689 A1 | 6/2006 | Albans et al. |
| 2006/0116690 A1 | 6/2006 | Pagano |
| 2006/0142795 A1 | 6/2006 | Nguyen et al. |
| 2006/0149268 A1 | 7/2006 | Truckai et al. |
| 2006/0155289 A1 | 7/2006 | Windhager et al. |
| 2006/0235451 A1 | 10/2006 | Schomer et al. |
| 2007/0027464 A1 | 2/2007 | Way et al. |
| 2007/0055259 A1 | 3/2007 | Norton et al. |
| 2007/0123877 A1 | 5/2007 | Goldin et al. |
| 2008/0114364 A1 | 5/2008 | Goldin et al. |

FOREIGN PATENT DOCUMENTS

| | | |
|---|---|---|
| EP | 0 442 137 | 8/1991 |
| EP | 0 748 615 | 12/1996 |
| WO | WO 90/07304 | 7/1990 |
| WO | WO 98/51226 | 11/1998 |
| WO | WO 2004/049961 | 6/2004 |

OTHER PUBLICATIONS

Office Action dated Jan. 21, 2010 for U.S. Appl. No. 11/140,413.
Office Action dated Dec. 7, 2009 for U.S. Appl. No. 10/818,452.

* cited by examiner

TRAUMA NAIL ACCUMULATOR

PRIORITY

This application claims priority to and benefit of U.S. Provisional Application No. 61/152,866, filed on Feb. 16, 2009, which is herein incorporated by reference in its entirety.

FIELD

Embodiments of the present invention relate, in general, to an accumulator device, and, in particular, to an accumulator that may store energy within an inflatable intramedullary rod.

BACKGROUND

To stabilize a bone fracture using an inflatable device, such as an inflatable intramedullary nail, the inflatable device may have to maintain a certain pressure for an extended period of time, which may include the duration of implantation. If such a pressure is not maintained, the bone fracture may not heal or it may malunion. Many things may affect the pressure in this closed system, which may include the inflatable nail and fracture cavity. For example, after a fracture is set and the inflatable device is sealed off during implantation, any expansion of the intramedullary canal or leakage from the device may cause the system pressure to drop. In another example, even slight expansion of an inflatable balloon nail or small losses of fluid at joints or bonds may influence the system pressure. If a system having no stored energy incurs such pressure losses, the pressure may drop immediately.

Thus, it may be advantageous to provide stored energy in an accumulator, which may supply energy, absorb pressure spikes, and stabilize a system during changes in fluid or cavity volume. The use of an accumulator may result in a system that is able to withstand greater volume losses or changes with a reduced effect on the system pressure. Such an accumulator may be located inside or outside an inflatable nail.

BRIEF DESCRIPTION OF THE DRAWINGS

The accompanying drawings incorporated in and forming a part of the specification illustrate several aspects of the present disclosure, and together with the description serve to explain the principles of the invention; it being understood, however, that the described embodiments are not limited to the precise arrangements shown. In the drawings, like reference numerals refer to like elements in the several views. In the drawings.

DETAILED DESCRIPTION

Versions of the present invention comprise an accumulator device that stores energy that may be released to help stabilize and maintain a system pressure. In one embodiment, the accumulator device may be located within an inflatable device, such that the pressure in a bone fracture cavity may be maintained. In another embodiment, the accumulator device may be attached externally to an inflatable device after implantation of the device. In still another embodiment, the inflatable device may be an intramedullary nail. A further embodiment involves an accumulator device comprising a piston. Such a piston accumulator may comprise a spring or compressed air as its energy source. Another embodiment involves an accumulator device comprising a pressurized bladder. In another embodiment, the lumen of the inflatable device may be flexible.

Figure 1:
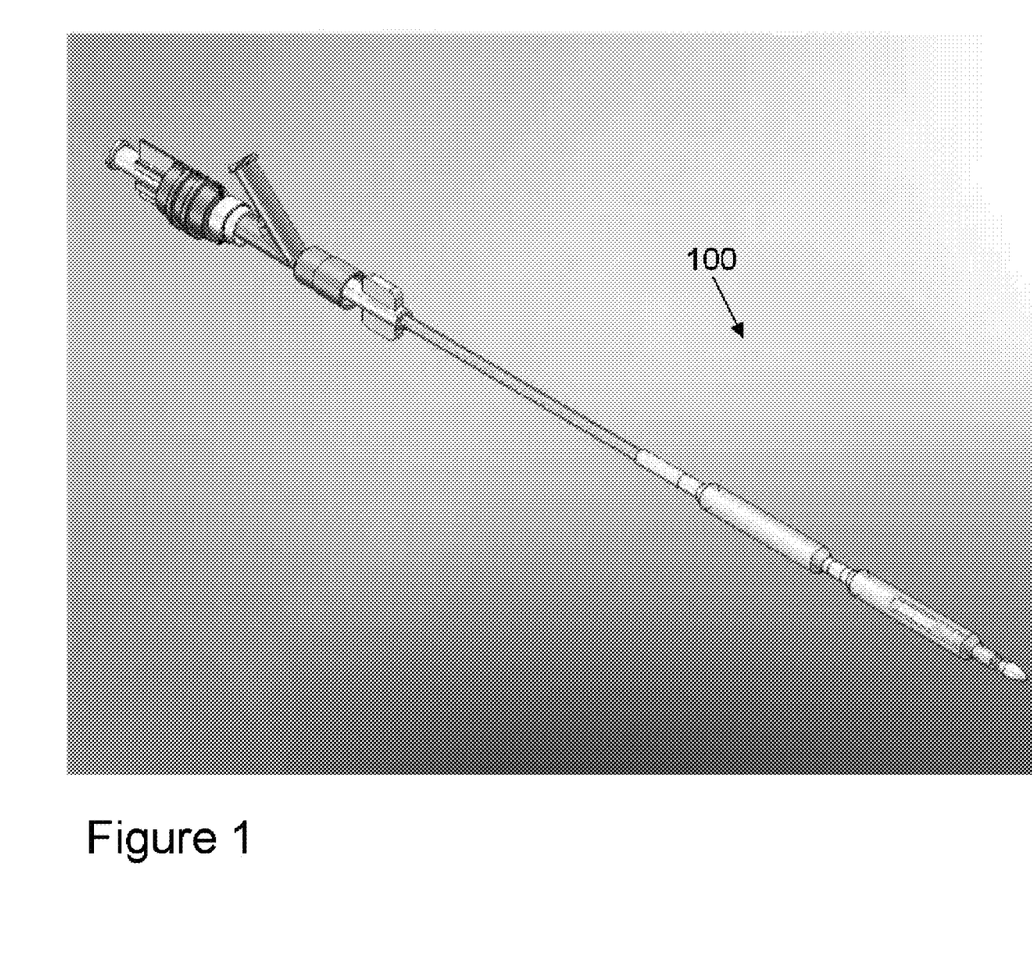
FIG. 1 is an isometric view of an exemplary inflatable nail device.
Figure 2:
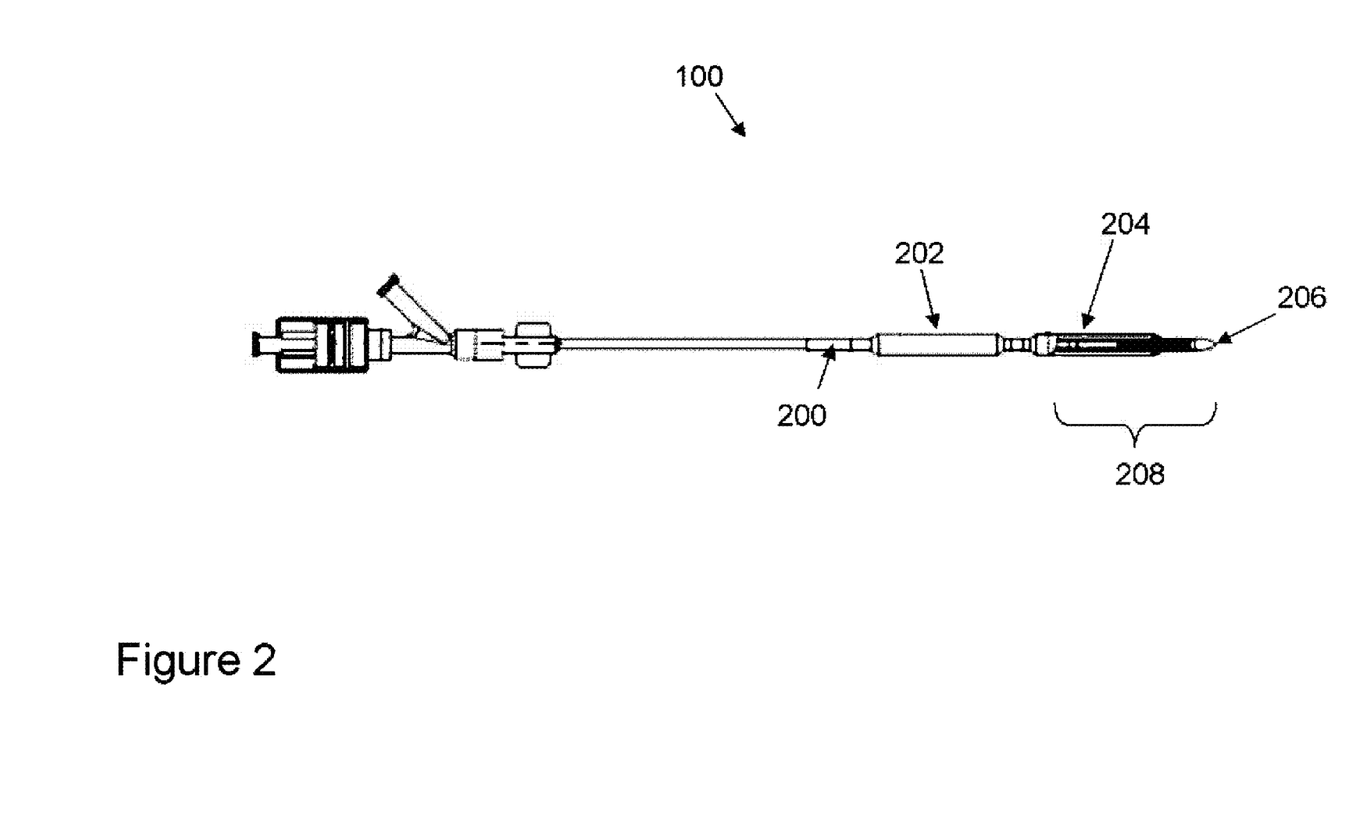
FIG. 2 is a front view of an exemplary inflatable nail device.

Referring to FIG. 1, one example of an inflatable device 100 is shown. The inflatable device 100 may be of any suitable configuration as will be apparent to one of ordinary skill in the art. For example, inflatable device 100 may be an inflatable nail. In another example, inflatable device 100 may be an inflatable intramedullary nail. In still another example, inflatable device 100 may be of a type disclosed in Goldin et al. (US 2007/0123877, published May 31, 2007). Referring to FIG. 2, another version of an inflatable device 100 is shown. As displayed in FIG. 2, inflatable device 100 may be an inflatable nail. An inflatable device 100 may comprise, for example, a nail shaft 200, a proximal balloon 202, a distal balloon 204, and a nail tip 206. Inflatable device 100 may also comprise an accumulator 208. Accumulator 208 may be internal or external to an inflatable device 100. For example, FIG. 2 shows an internal accumulator 208.

Figure 3:
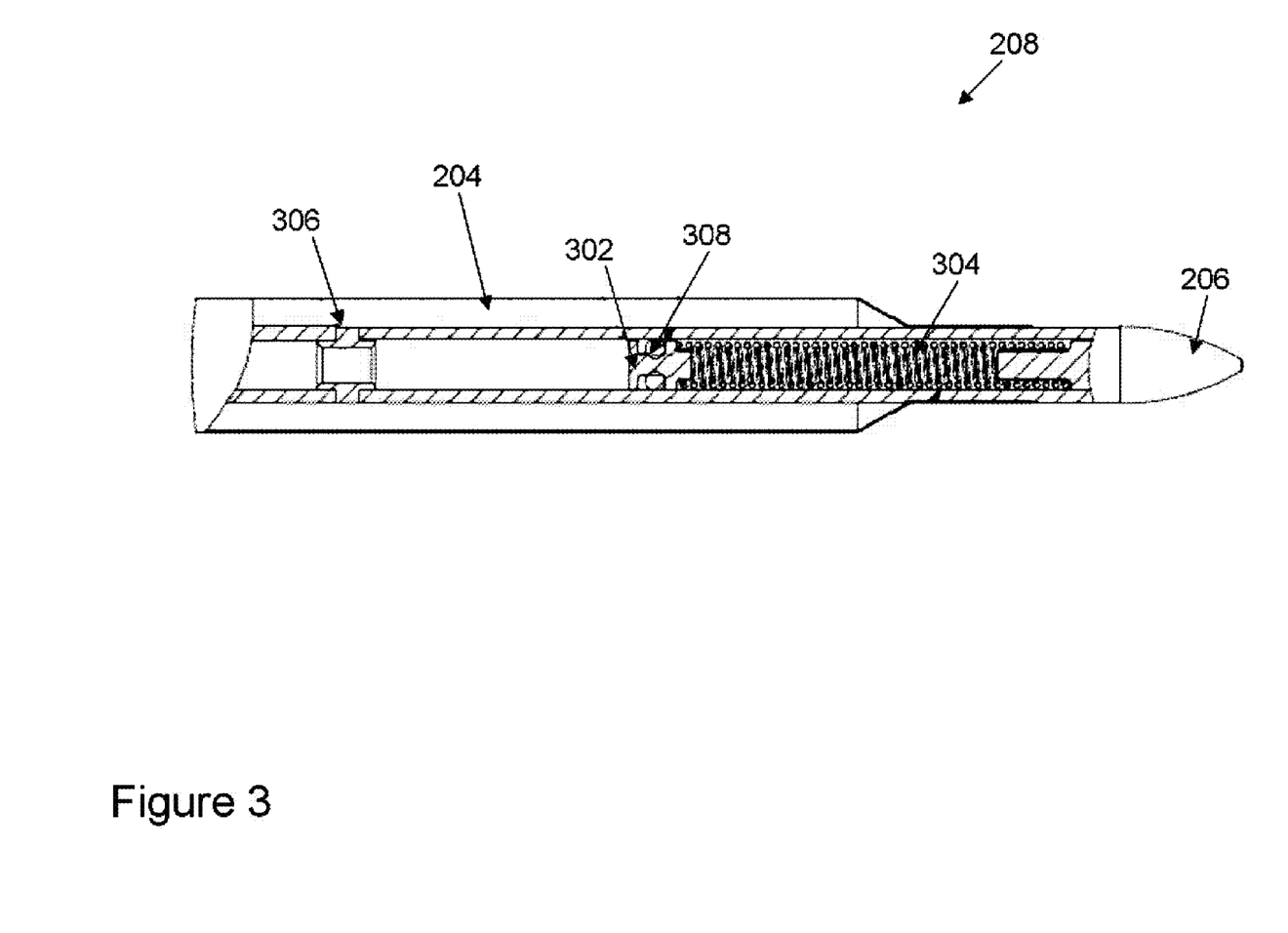
FIG. 3 is a front view of an exemplary internal piston accumulator device.

Referring to FIG. 3, one example of an accumulator 208 is shown. In this example, accumulator 208 is located within an inflatable device 100. Specifically, FIG. 3 shows accumulator 208 located within a nail shaft 200. Accumulator 208 may comprise any number of parts as will be apparent to one of ordinary skill in the art. For example, the internal accumulator 208 shown in FIG. 3 comprises a piston 302. In the alternative, internal accumulator 208 may comprise a pressurized bladder (not pictured in FIG. 3). Accumulator 208 may also comprise an energy source 304. Energy source 304 may be any source capable of being compressed as will be apparent to one of ordinary skill in the art. For example, energy source 304 may be a spring or compressed air. An accumulator 208 may be mechanical or hydro-pneumatic, depending on the energy source 304. For example, a mechanical accumulator 208 may comprise a piston 302 that compresses a spring 304 to provide energy to the system. In another example, a hydro-pneumatic accumulator 208 may comprise a piston 302 that compresses air 304 to provide energy to the system. Accumulator 208 may also comprise an orifice 306. Orifice 306 may comprise any suitable means to adjust the fluid flow in accumulator 208. For example, orifice 306 may be an adjustable valve. In another example, as shown in FIG. 3, orifice 306 may be a coupler located between nail shaft 200 and the body of accumulator 208. A seal 308 may seal piston 302 from a fluid leak. For example, seal 308 may prevent fluid used to inflate distal balloon 204 from leaking into energy source 304. Seal 308 may be produced by any suitable means as will be apparent to one of ordinary skill in the art. For example, an o-ring may comprise seal 308.

Figure 4:
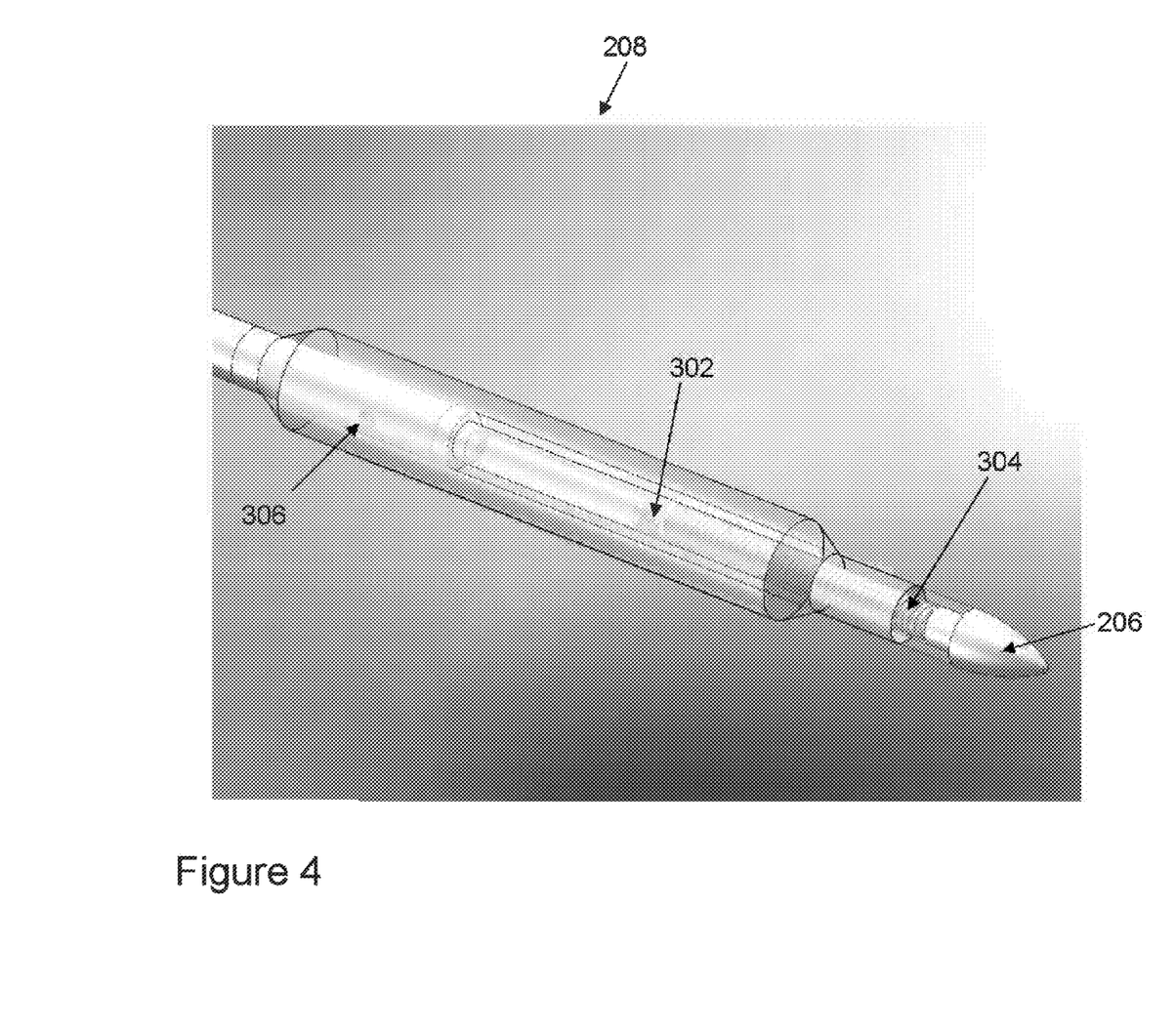
FIG. 4 is an isometric view of an exemplary internal piston accumulator device.

Referring to FIG. 4, another example of an internal accumulator 208 is shown. In this example, accumulator 208 comprises a piston 302 and a spring 304. An accumulator 208 may compensate for a change in system volume or pressure to help maintain a stable pressurized system. For example, a piston 302 may translate within a nail shaft 200, remaining in contact with spring 304. In this way, when a system is pressurized, piston 302 may exert a force on energy source 304, causing it to compress. For example, after insertion of an inflatable device 100 and inflation of a balloon 202 or 204, piston 302, which may be exposed to the internal hydraulic pressure of device 100 via orifice 306, may compress energy source 304, which stores energy. A piston 302 may compress energy source 304 until the pressure of the energy source 304 and the system pressure equalize or until energy source 304 is fully compressed. While inflatable device 100 is implanted or otherwise in use, accumulator 208 may compensate for losses or changes in the pressure or volume of the system to maintain a stable pressure in the system. For example, accumulator 208 may stabilize pressure or volume by supplying fluid to the closed system. In another example, a change in system pressure may cause the fluid pressure exerted on piston 302 to lessen, which may simultaneously lessen the compression force piston 302 exerts on energy source 304. In this way, energy source 304 may extend or expand to take up the space of the lost fluid, and therefore minimize system pressure loss. In another embodiment (not pictured), an internal accumulator may comprise two separate chambers, and therefore two pistons and two orifices. Such an accumulator may have a single spring, which equalizes the system pressure between each chamber.

Figure 5:
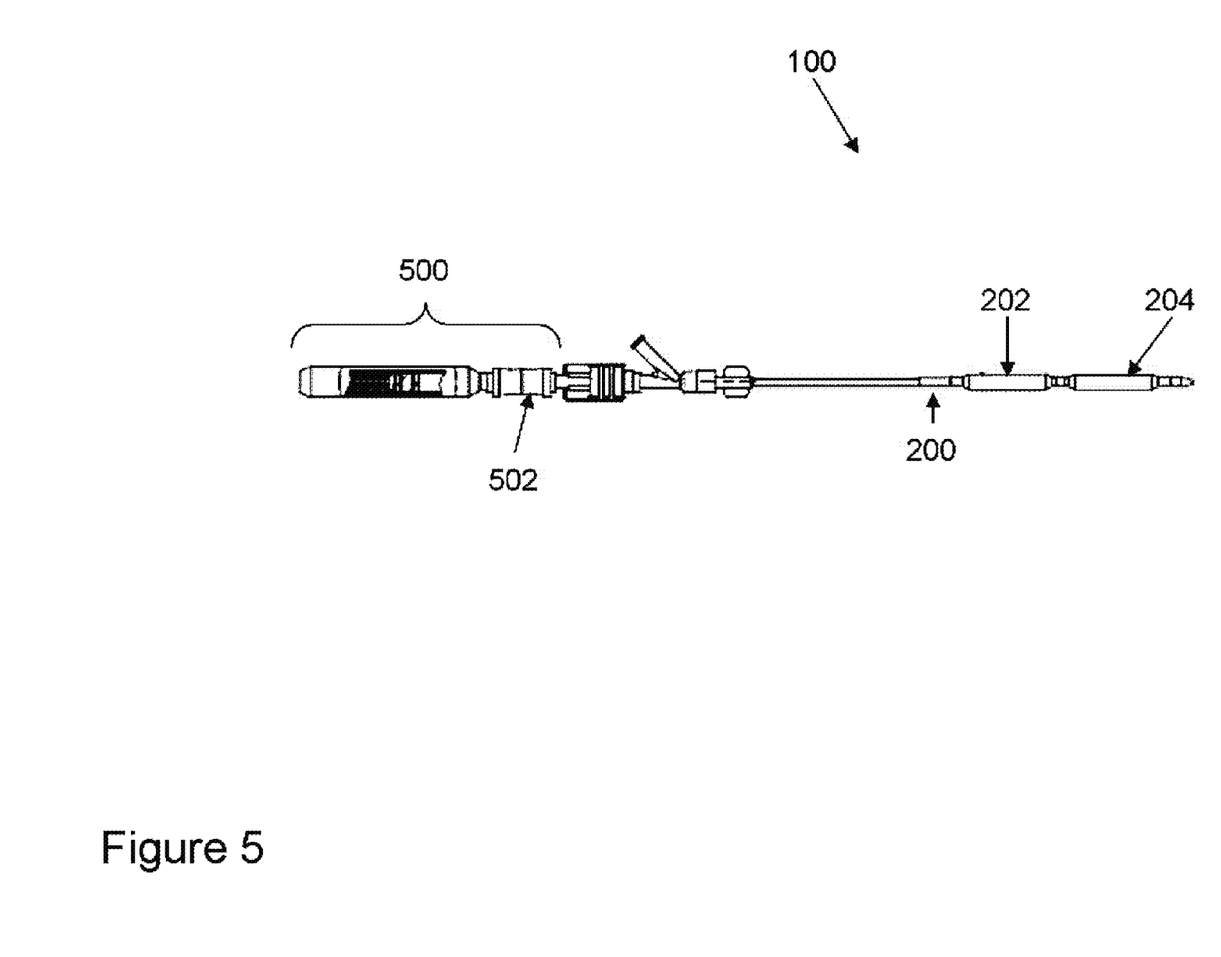
FIG. 5 is a front view of an exemplary inflatable nail device.
Figure 6:
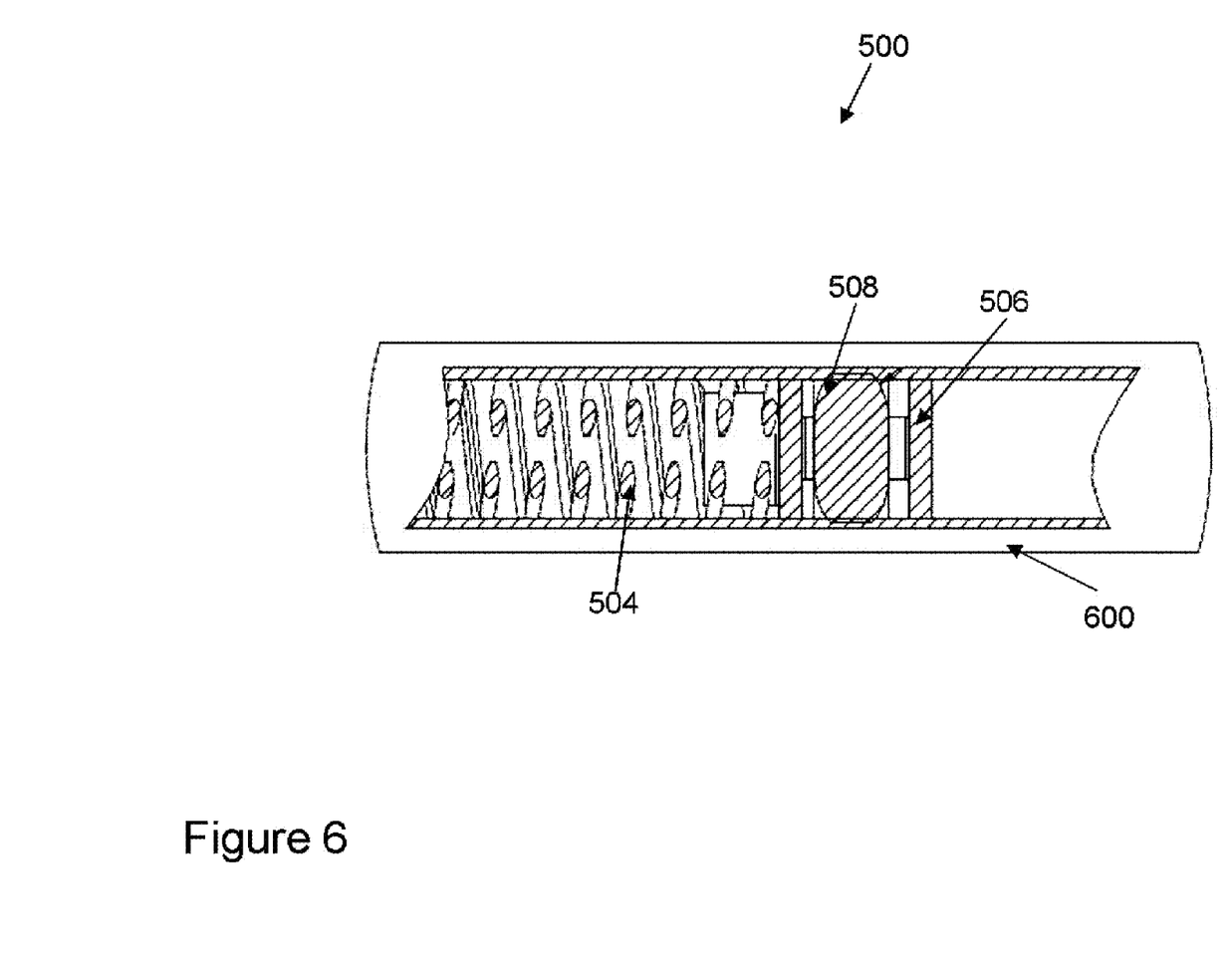
FIG. 6 is a front view of an exemplary external piston accumulator device.

In another embodiment, an accumulator may be external to an inflatable device 100. Referring to FIG. 5, such an inflatable device 100 and an external accumulator 500 is shown. In FIG. 5, the inflatable device 100 is a nail having a shaft 200, a proximal balloon 202, and a distal balloon 204. Rather than being located within the inflatable nail 100, accumulator 500 may be located outside the nail 100. Referring to FIG. 6, another example of an external accumulator 500 is shown. In this example, accumulator 500 comprises an orifice 502, an energy source 504, a piston 506, and a seal 508. An orifice 502 may comprise any suitable means to adjust the fluid flow in the accumulator 500. For example, orifice 502 may be an adjustable valve. In another example, as shown in FIG. 6, orifice 502 may be a coupler located between nail shaft 200 and the body of accumulator 500. Energy source 504 may be any source capable of being compressed as will be apparent to one of ordinary skill in the art. For example, energy source 504 may be a spring or compressed air. An external accumulator 500 may be mechanical or hydro-pneumatic, depending on the energy source 504. For example, a mechanical accumulator 500 may comprise a piston 506 that compresses a spring 504 to provide energy to the system. In another example, a hydro-pneumatic accumulator 500 may comprise a piston 506 that compresses air 504 to provide energy to the system. A seal 508 may seal piston 506 from a fluid leak. For example, seal 508 may prevent fluid used to inflate distal balloon 204 from leaking into energy source 504. Seal 508 may be produced by any suitable means as will be apparent to one of ordinary skill in the art. For example, an o-ring may comprise seal 508.

External accumulator 500 may compensate for a change in system volume or pressure in a similar manner as internal accumulator 208. For example, piston 506 may translate within a separate housing 600, remaining in contact with energy source 504, which in this example is a spring. In this way, when a system is pressurized, piston 506 may exert a force on energy source 504, causing it to compress. For example, after insertion of an inflatable device 100 and inflation of a balloon 202 or 204, piston 506, which may be exposed to the internal hydraulic pressure of device 100 via orifice 502, may compress energy source 504. Piston 506 may compress energy source 504 until the pressure of the energy source 504 and the system pressure equalize or until energy source 504 is fully compressed. While inflatable device 100 is implanted or otherwise in use, accumulator 500 may compensate for losses or changes in the pressure or volume of the system to maintain a stable pressure in the system. For example, accumulator 500 may stabilize pressure or volume by supplying fluid to the closed system. In another example, a change in system pressure may cause the fluid pressure exerted on piston 506 to lessen, which may simultaneously lessen the compression force piston 506 exerts on energy source 504. In this way, energy source 504 may extend or expand to take up the space of the lost fluid, and therefore minimize system pressure loss. In another embodiment (not pictured), an external accumulator may comprise two separate chambers, and therefore two pistons and two orifices. Such an accumulator may have a single spring, which equalizes the system pressure between each chamber.

Figure 7:
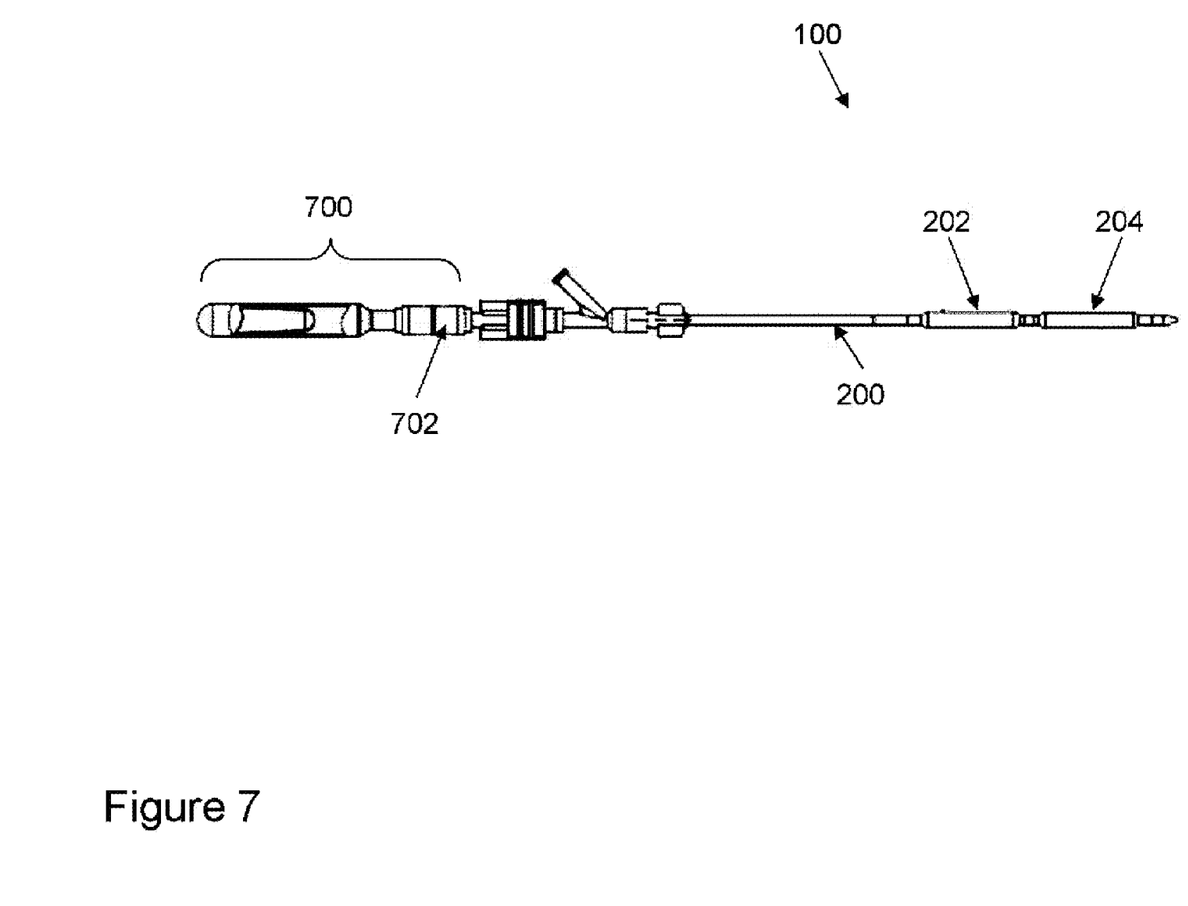
FIG. 7 is a front view of an exemplary inflatable nail device.
Figure 8:
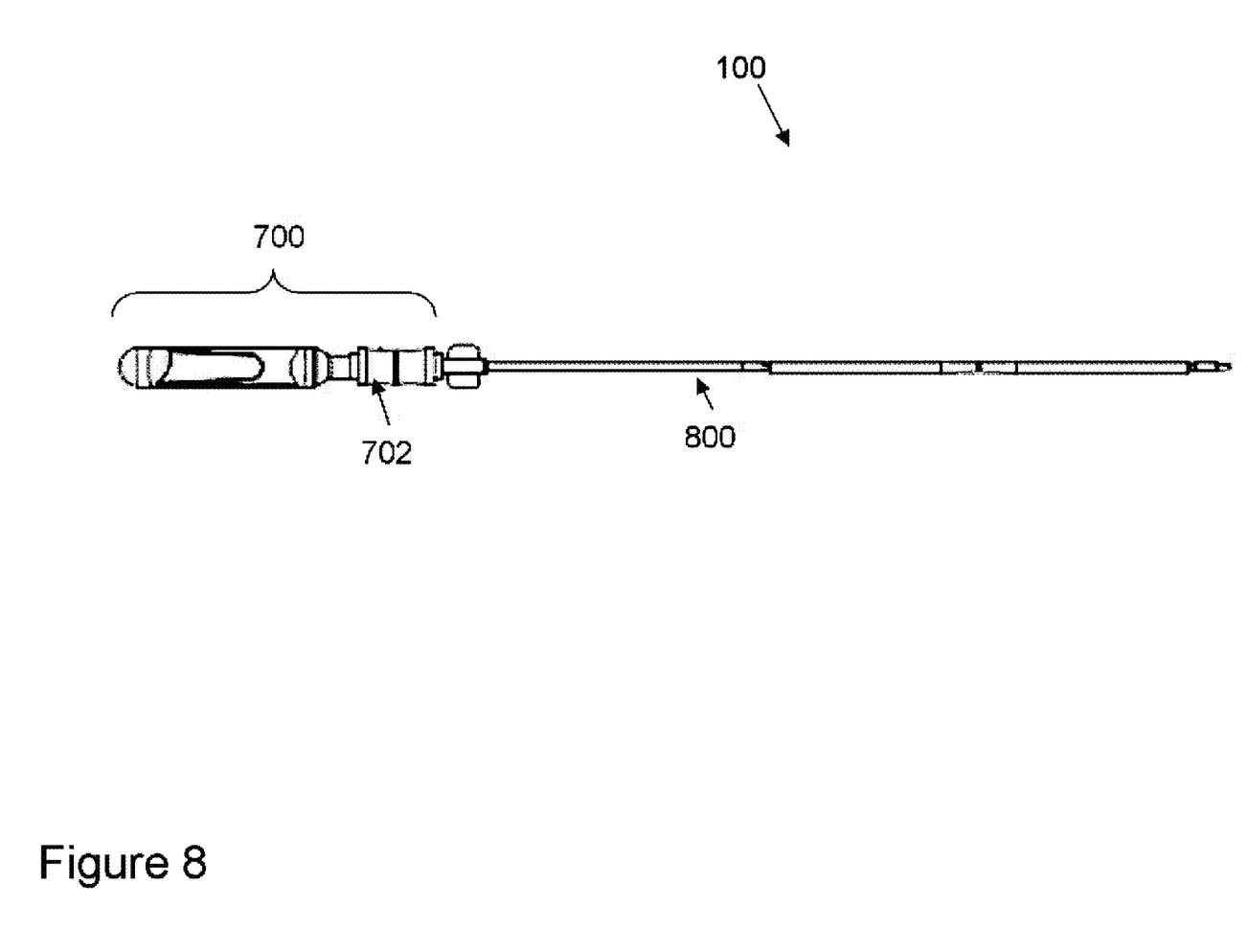
FIG. 8 is a front view of an exemplary inflatable nail device.

In an alternative embodiment, an accumulator may comprise a pressurized bladder instead of a piston. Referring to FIG. 7, a bladder accumulator 700 is shown. Bladder accumulator 700 may be internal or external to an inflatable device 100. In FIG. 7, bladder accumulator 700 is shown external to inflatable device 100. In this embodiment, inflatable device 100 may be an inflatable nail, as shown in FIG. 7. Inflatable device 100 may comprise, for example, a nail shaft 200, a proximal balloon 202, and a distal balloon 204. Referring to FIG. 8, an external bladder accumulator 700 is shown with another inflatable device 100. In this example, inflatable device 100 is a single lumen nail. The single lumen nail may have a nail shaft 800.

Figure 9:
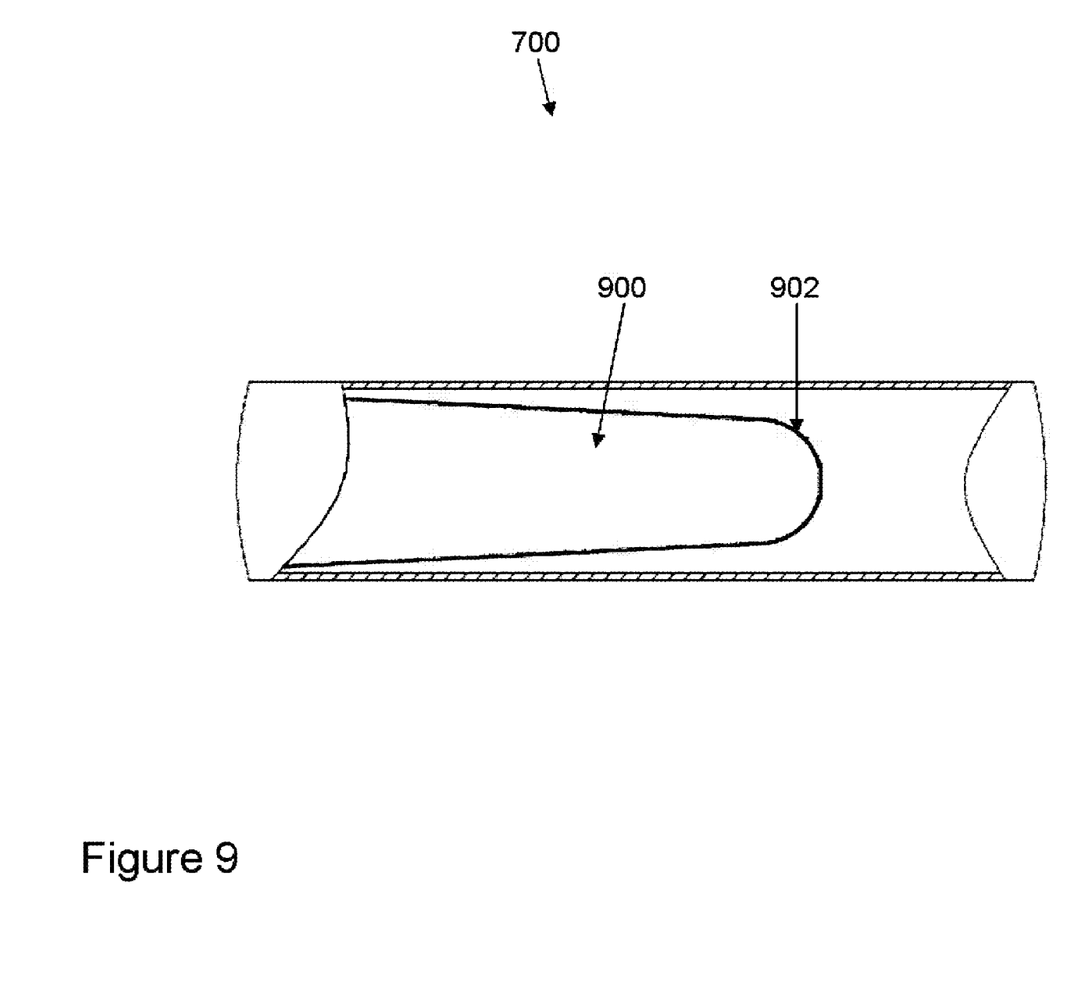
FIG. 9 is a front view of an exemplary external bladder accumulator device.

Referring to FIG. 9, another example of a bladder accumulator 700 is shown. Bladder accumulator 700 may comprise, for example, an orifice 702, an energy source 900, and a bladder 902. Orifice 702 may comprise any suitable means to adjust the fluid flow in accumulator 700. For example, orifice 702 may be an adjustable valve. In another example, as shown in FIGS. 7-8, orifice 702 may be a coupler located between nail shaft 200 and/or 800 and the body of accumulator 700. Energy source 900 may be comprised of a pressurized or compressed gas within a bladder 902. The compressed gas may be, for example, nitrogen. Bladder accumulator 700 may also compensate for a change in system volume or pressure. In a bladder accumulator 700, the fluid used to inflate an inflatable device 100 may exert a force against an energy source 900, compressing the gas within bladder 902 and pressurizing it further. If the system loses pressure, the pressurized bladder 902 may expand, take up the room of the lost fluid, and thereby maintain the system pressure.

Figure 10:
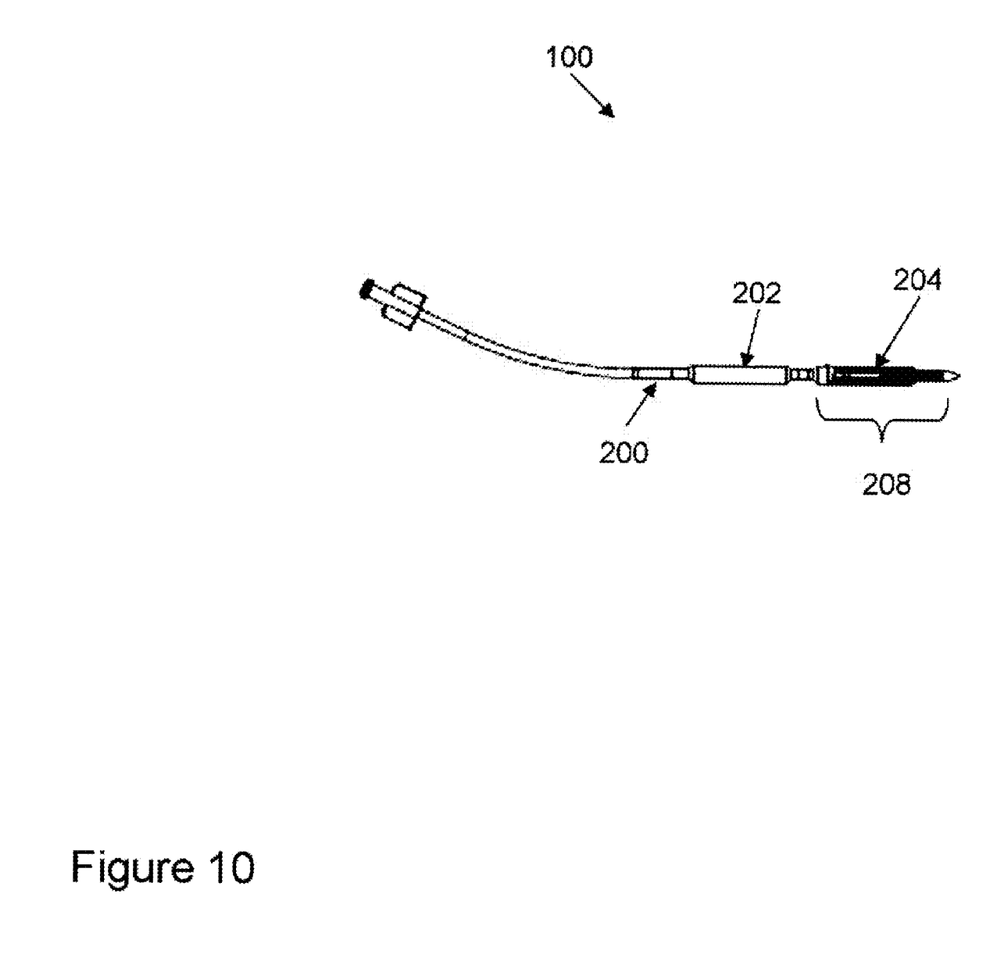
FIG. 10 is a front view of an exemplary flexible lumen inflatable nail device.

Referring to FIG. 10, another embodiment of an accumulator device is shown. In this embodiment, inflatable device 100 may comprise an inflatable nail and a flexible lumen. Such a flexible lumen may, for example, ease the implantation of the inflatable nail. In the figure, the flexible lumen inflatable device 100 includes an internal accumulator 208. A flexible lumen inflatable device 100, however, may be used in conjunction with any of the other embodiments described in this application as will be apparent to one of ordinary skill in the art. For example, a flexible lumen inflatable device 100 may be combined with an external accumulator, an internal or external piston accumulator, and/or an internal or external bladder accumulator.

The versions presented in this disclosure are examples. Those skilled in the art can develop modifications and variants that do not depart from the spirit and scope of the accumulator device. Thus, the scope of the invention should be determined by appended claims and their legal equivalents, rather than by the examples given.

What is claimed is:

1. An apparatus for maintaining a pressure level in a closed system, the apparatus comprising:
   (a) a means for providing energy to the system, the means for providing energy being capable of moving between a contracted state and an expanded state in reaction to an outside force;
   (b) a means for providing the outside force that can be positioned in a first position and a second position, wherein positioning the means for providing the outside force from the first position to the second position causes the means for providing energy to move to maintain a system pressure level.

2. The apparatus of claim 1, further comprising a means for adjusting fluid flow in the apparatus.

3. The apparatus of claim 2, wherein the apparatus is coupled with a device comprising at least one inflatable balloon, the device being insertable into a bone cavity.

4. The apparatus of claim 3, wherein the apparatus is externally coupled with the device.

5. The apparatus of claim 3, wherein the apparatus is internally coupled with the device.

6. The apparatus of claim 3, wherein the means for providing energy is a mechanism selected from the group consisting of a spring and a volume of compressed air.

7. The apparatus of claim 6, wherein the means for providing the outside force is a piston, the translation of the piston between the first position and the second position causing the mechanism selected from the group consisting of a spring and a volume of compressed air to move to maintain a constant pressure in the closed system.

8. The apparatus of claim 6, wherein the means for providing the outside force is a gas-filled bladder that can be expanded or contracted, the expansion and contraction of the bladder causing the mechanism selected from the group consisting of a spring and a volume of compressed air to move to maintain a constant pressure in the closed system.

9. The apparatus of claim 8, wherein the gas-filled bladder further comprises nitrogen.

10. The apparatus of claim 2, wherein the means for adjusting fluid flow is a mechanism selected from the group consisting of an adjustable valve and a coupler.

11. An inflatable device that maintains a system pressure in a bone cavity, the inflatable device comprising:
    (a) at least one inflatable balloon; and
    (b) an accumulator device in fluid communication with the at least one inflatable balloon, the accumulator device comprising
       a source of energy moveable between a contracted state and an expanded state; and
       a pressurized apparatus that can be positioned in a first position and a second position, wherein positioning the pressurized apparatus from the first position to the second position causes the source of energy to move to maintain a pressure level.

12. The inflatable device of claim 11, wherein the device is an inflatable nail.

13. The inflatable device of claim 12, wherein the device is an inflatable intramedullary nail.

14. The inflatable device of claim 11, wherein the accumulator is positioned in a housing external to the at least one inflatable balloon.

15. The inflatable device of claim 11, wherein the at least one inflatable balloon is positioned within a housing, and wherein the accumulator is positioned in the housing along with the at least one inflatable balloon.

16. The inflatable device of claim 15, wherein the device is an inflatable nail having an inner shaft, and wherein the accumulator is positioned within a nail shaft of the device.

17. The inflatable device of claim 12, further comprising a flexible lumen to ease the insertion of the inflatable nail.

18. A method of maintaining a stable pressurized system in a bone cavity, comprising:
    providing an inflatable device, the inflatable device comprising:
       (a) at least one inflatable balloon; and
       (b) an accumulator device in fluid communication with the at least one inflatable balloon, the accumulator device comprising
          a source of energy moveable between a contracted state and an expanded state; and
          a pressurized apparatus that can be positioned in a first position and a second position, wherein positioning the pressurized apparatus from the first position to the second position causes the source of energy to move to maintain a pressure level;
    inserting the inflatable device into a bone cavity; inflating the at least one inflatable balloon to a certain pressure;
    moving the pressurized apparatus from a first position to a second position to cause energy to be stored within the source of energy; and
    releasing the energy stored within the source of energy to maintain the certain pressure in the bone cavity.

19. The method of claim 18, wherein the inflatable device is an intramedullary nail.

* * * * *